United States Patent
Boujtita et al.

(10) Patent No.: US 10,385,466 B2
(45) Date of Patent: Aug. 20, 2019

(54) DEVICE AND METHOD FOR ELECTROCHEMICALLY SYNTHESIZING INTERMEDIATE SPECIES OF A CHEMICAL ENTITY

(71) Applicants: CENTRE NATIONAL DE LA RECHERCHE SCIENTIFIQUE (C.N.R.S.), Paris (FR); UNIVERSITE DE NANTES, Nantes (FR)

(72) Inventors: Mohammed Boujtita, Nantes (FR); Ugo Bussy, Nantes (FR)

(73) Assignees: CENTRE NATIONALE DE LA RECHERCHE SCIENTIFIQUE (C.N.R.S), Paris (FR); UNIVERSITE DE NANTES, Nantes (FR)

( * ) Notice: Subject to any disclaimer, the term of this patent is extended or adjusted under 35 U.S.C. 154(b) by 1000 days.

(21) Appl. No.: 14/759,344

(22) PCT Filed: Jan. 6, 2014

(86) PCT No.: PCT/EP2014/050098
§ 371 (c)(1),
(2) Date: Nov. 6, 2015

(87) PCT Pub. No.: WO2014/108372
PCT Pub. Date: Jul. 17, 2014

(65) Prior Publication Data
US 2016/0053389 A1    Feb. 25, 2016

(30) Foreign Application Priority Data
Jan. 8, 2013    (FR) ..................................... 13 50154

(51) Int. Cl.
C25B 15/08    (2006.01)
C25B 9/00    (2006.01)
(Continued)

(52) U.S. Cl.
CPC .................. *C25B 9/18* (2013.01); *C25B 3/02* (2013.01); *C25B 3/04* (2013.01); *C25B 11/02* (2013.01);
(Continued)

(58) Field of Classification Search
CPC .. C25B 1/46; C25B 1/00; C25B 15/08; C25B 3/02; C25B 9/06; C25B 9/18; C25B 9/00; C25B 3/04; C25B 9/04
(Continued)

(56) References Cited

U.S. PATENT DOCUMENTS 4,133,726 A    1/1979    Wagenknecht et al.
4,511,659 A    4/1985    Matson
(Continued)

FOREIGN PATENT DOCUMENTS

WO    9741429 A1    11/1997
WO    03081208 A2    10/2003
WO    2014-108372 A1    7/2014

OTHER PUBLICATIONS

French Search Report dated Oct. 4, 2013 issued during prosecution of French Application No. FR1350154.
(Continued)

*Primary Examiner* — Zulmariam Mendez
(74) *Attorney, Agent, or Firm* — Troutman Sanders LLP

(57) ABSTRACT

The device for electrochemically synthesizing intermediate species of a chemical entity which comprises an electrochemical oxidation cell including a first working electrode and a first counter electrode, capable, when these first electrodes are subject to an electric potential, of generating the intermediate species by oxidation of a solution introduced into the electrochemical oxidation cell and comprising the chemical entity, and an electrochemical stabilization cell including a second working electrode and a second
(Continued)

counter electrode respectively distinct from the first working electrode and counter electrode, capable, when these second electrodes are subject to an electric potential, of achieving reduction of a solution. The stabilization cell is connected in series to the oxidation cell so as to allow continuous reduction of the intermediate species generated in the oxidation cell. Applications can be in the pharmaceutical, agri-food and environment fields.

11 Claims, 1 Drawing Sheet

(51) Int. Cl.
    *C25B 9/04*       (2006.01)
    *C25B 9/18*       (2006.01)
    *G01N 33/00*     (2006.01)
    *C25B 3/02*       (2006.01)
    *C25B 3/04*       (2006.01)
    *C25B 11/02*     (2006.01)
    *G01N 30/72*     (2006.01)
    *G01N 30/88*     (2006.01)

(52) U.S. Cl.
    CPC ..... *G01N 33/0013* (2013.01); *G01N 30/7266* (2013.01); *G01N 2030/8813* (2013.01)

(58) Field of Classification Search
USPC .......................................................... 205/345
See application file for complete search history.

(56) References Cited

U.S. PATENT DOCUMENTS 5,154,895 A * 10/1992 Moon .................. A23L 3/3409
                                            422/186.07
2008/0073288 A1* 3/2008 Fan ....................... C02F 1/4691
                                                 204/554

OTHER PUBLICATIONS

Baumann et al. "Online Electrochemistry/Mass Spectrometry in Drug Metabolism Studies: Principles and Applications," University of Munster 6:715-731 (2010).

Lohmann et al. "On-Line Electrochemistry/Liquid Chromatography/Mass Spectrometry for the Simulation of Pesticide Metabolism," Journal of the American Society for Mass Spectrometry, vol. 20 Issue 1:138-145 (2009).

* cited by examiner

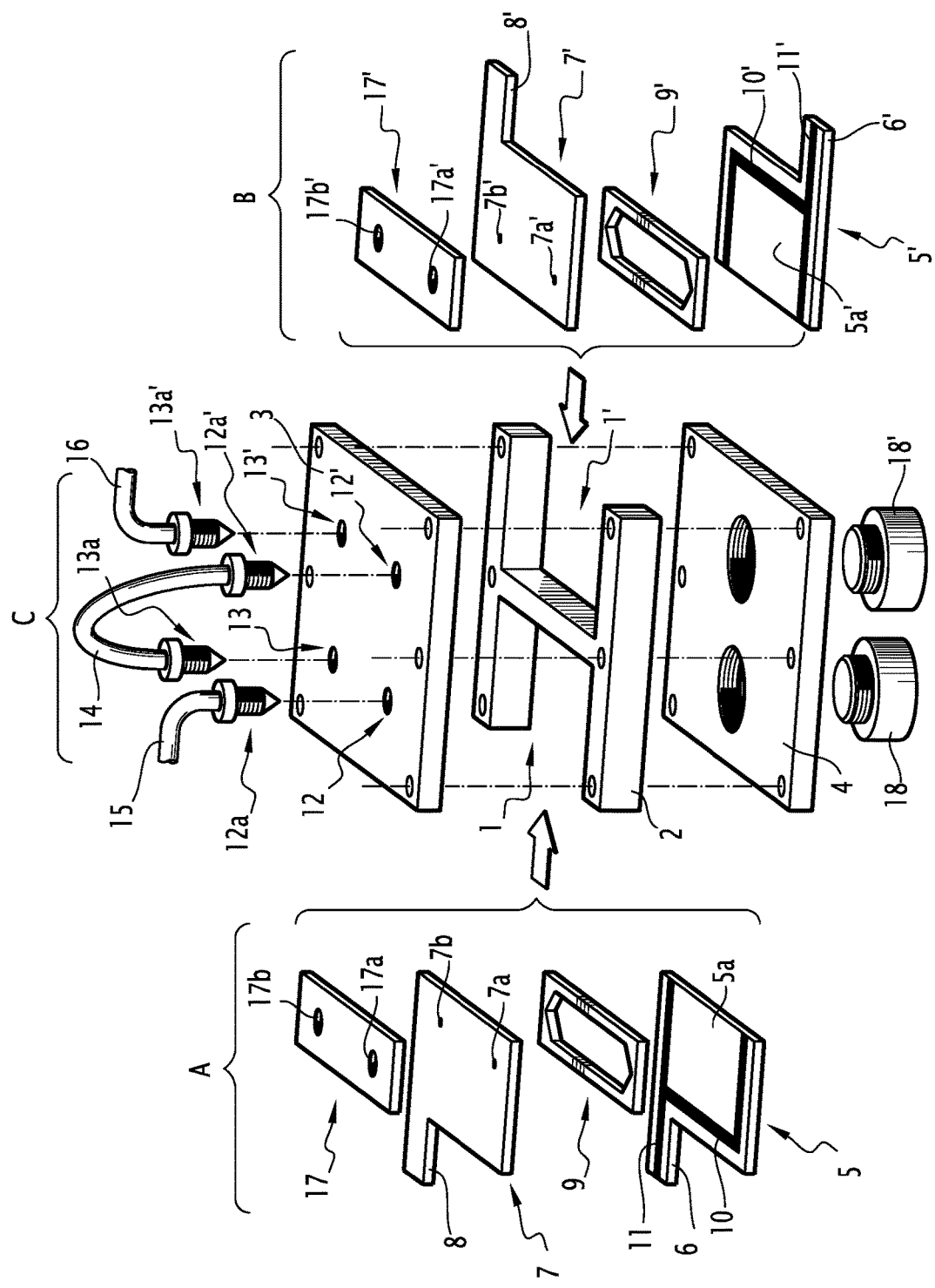

DEVICE AND METHOD FOR ELECTROCHEMICALLY SYNTHESIZING INTERMEDIATE SPECIES OF A CHEMICAL ENTITY

CROSS-REFERENCE TO RELATED APPLICATIONS

The present application is a National Stage of International Application PCT/EP2014/050098 filed Jan. 6, 2014. The International Application claims priority to a French Patent Application No. 13 50154 filed Jan. 8, 2013. The International Application published as WO/2014/108372 on Jul. 17, 2014. All of the above applications are incorporated by reference herein.

FIELD OF THE INVENTION

The present invention relates to a device and to a method for electrochemically synthesizing intermediate species such as metabolites.

BACKGROUND

The invention finds application in the field of structural identification of oxidation products, for example by mass spectrometry, NMR, infrared. Notably, in the pharmaceutical field, the invention applies to the making of pharmacological and toxicological tests, more specifically for studying the oxidative fate of certain drugs with view to evaluating the stability, the chemical activity and the biological reactivity of the main intermediate species. Also, in the field of the agri-food industry, the invention applies to elucidation of oxidative or photo-oxidative degradation of food additives such as preservatives, coloring agents, anti-oxidants. In further another field, that of the environment, the invention applies to predicting the fate of emerging pollutants like drugs, detergents, phenol derivatives.

Prediction of risks posed by many chemical entities (such as xenobiotics) for human health and its environment is today considered as a major social issue. Many xenobiotics like drugs, emergent pollutants, pesticides, preservatives, food additives and other substances, have shown that they may cause major secondary effects, as testified by examples of withdrawal of certain drugs, food preservatives and plant protection products on the market.

In this context, the development of novel analytic tools in vitro mimicking oxidative metabolism is presently an emerging axis of vital investigation for predicting possible toxic effects of chemical species. These novel tools are essentially based on the prediction of oxidative degradation schemes which a xenobiotic may undergo (Donato, M. T.; Castell, J. V.; Gomez-Lechon, M. J., Characterization of drug metabolizing activities in pig hepatocytes for use in bioartificial liver devices: comparison with other hepatic cellular models. Journal of Hepatology 1999, 31, (3), 542-549; Dong H., Haining, R. L., Thummel, K. E.; Rettie, A. E.; Nelson, S. D.; Involvement of human cytochrome p450 2D6 in the bioactivation of acetaminophen. Drug Metab Dispos 2000, 28, (12), 1397-400; Ferchaud, V; Le, B. B., Montrade, M-P.; Maume, D.; Monteau, F.; André, F., Gas chromatographic-mass spectrometric identification of main metabolites of stanozolol in cattle after oral and subcutaneous administration. J. Chromatogr., B Biomed. Sci Appl. 1997, 695, (2) 269-277).

Several biological models used in vitro have been explored for studying oxidative metabolization of xenobiotics (Henderson, M. C, Siddens, L. K, Morré, J. T, Krueger, S. K, Williams, D. E. Metabolism of the anti-tuberculosis drug ethionamide by mouse and human FMO1, FMO2 and FMO3 and mouse and human lung microsomes. Toxicology and Applied Pharmacology 2008, 233, (3), 420-427; Yun, C-H. Miller, G. P, Guengerich, F. P. Rate-Determining Steps in Phenacetin Oxidations by Human Cytochrome P450 1A2 and Selected Mutants. Biochemistry 200, 39, (37), 11319-11329).

For example mention may be made of the use of liver sections for studying certain metabolisms with view to identifying different metabolites. The use of hepatocytes, today commercially available, has also been highly successful in this field.

Further, by the development of molecular biology and the launching on the market of many recombinant enzymes, a more significant preference is today described for using enzymes from the family of P450 cytochromes (Dong H., Haining, R. L., Thummel, K. E.; Rettie, A. E.; Nelson, S. D.; involvement of human cytochrome p450 2D6 in the bioactivation of acetaminophen. Drug Metab Dispos 2000, 28, (12), 1397-400; Anzenbacher, P. Anzenbacherova, E. Cytochromes P450 and metabolism of xenobiotics. Celle. Mol. Life Sci. 2001, 58, (5/6), 737-747; Delaforge, M. Pruvost, A. Perrin, L. Andre, F. Cytochrome P450-mediated oxidation of glucuronide derivatives: example of estradiol-17î²-glucuronide oxidation to 2-hydroxy-estrdiol-17î²-glucuronide by CYP 2C8 Drug Metab Dispos 2005, 33, (3), 466-473; Isin, E. M. Guengerich, F. P., Complex reactions catalyzed by cytochrome P450 enzymes Biochimica and Biophysica Acta (BBA)—General Subjects 2007, 1770, (3), 314-329).

These biological models are considered as tools of choice for studying oxidative metabolism; they not only give the possibility of providing a new understanding of the oxidative routes, but also of elucidating the mode of action or explaining the reasons of a possible toxicity of a chemical entity. These tests in vitro, of highly widespread use in the pharmaceutical industry and in many research laboratories, are simplified models as compared with tests in vivo, and give the possibility of setting up bases of experimental models in vivo, notably in the case of development of candidate drugs, and in the case of studying the effects of emerging pollutants on human health and on the environment.

It should also be noted that the development of tests in vitro in the field of oxidative degradation during the last decade also owes its success to the development of analytic instrumentation within these tests themselves, with the use of techniques such as extraction techniques (SPE), increasingly performing columns, HPLC coupling and mass spectrometry.

However, their advantage does not annihilate certain constraints inherent to the techniques used in vitro: slow analysis, difficulty of structurally characterizing the intermediate species stemming from the oxidative degradation of a xenobiotic (small generated amounts), low compatibility of organic solvents (solubilization of xenobiotics) with the use of biological materials (cells, enzymes and other materials) . . . .

Some of these problems were circumvented by using chemical methods (Chorghade, M. S.; Hill, D. R.; Lee, E. C.; Pariza, R. J.; Dolphin, D. H.; Hino, F.; Zhang, L.-Y., Metalloporphyrins as chemical mimics of cytochrome P-450 systems. Pure Appl. Chem. 1996, 68, (3), 753-756) and electrochemical methods (Karst, U.; Diehl, G.; Hayen, H. Coupling electrochemistry to mass spectrometry and high performance liquid chromatography. 2003; Karst, U., Analytical methods: Electrochemistry/mass spectrometry (EC/MS)—a new tool to study drug metabolism and reaction mechanisms. Angew. Chem., Int. Ed. 2004, 43, (19), 2476-2478).

Indeed, it has been shown that a conventional electrochemical cell (EC) with three electrodes associated with the performances of liquid phase chromatography (LC) and of mass spectrometry (EC-LC-MS coupling) may mimic certain reactions of oxidative metabolism, notably those initiated and catalyzed by the family of P450 cytochromes, such as for example N-dealkylation, O-dealkylation, epoxidization, oxidation of thiols, of alcohols, dehydrogenation of aromatic rings (Nouri-Nigjeh, E. Permentier, H. P. Bischoff, R. Bruins, A. P., Electrochemical Oxidation by Square-Wave Potential Pulses in the Imitation of Oxidative Drug Metabolism. Anal. Chem. 2011, (83), 14, 5519. Nouri-Nigjeh, E. Bruins, A. P. Bischoff, R. Permentier, H. P., Electrocatalytic oxidation of hydrogen peroxide on a platinum electrode in the imitation of oxidative drug metabolism of lidocaine. Analyst. 2012, (137), 4698.).

However, many points still remain to be explored. For example, we notice a lack of a device for synthesizing in a sufficient amount and under a stable condition main intermediate species from oxidative degradation of a xenobiotic. This limits the use of NMR on the one hand for elucidating with more accuracy the chemical structure of the different species, and the application of tests for predetermining the threshold concentration for evaluating the inhibition or toxic potential of the main species from oxidation of a xenobiotic on the other hand.

One of the objects of the invention is therefore to provide a solution to the aforementioned problems and drawbacks.

The invention thus according to a first aspect relates to a device for synthesizing intermediate species of a chemical entity, electrochemically.

SUMMARY

The device comprises an electrochemical oxidation cell which at least includes a first working electrode. Each electrochemical oxidation cell is capable, when the first working electrode is subject to an electric potential, of generating the intermediate species by oxidation of a solution introduced into the electrochemical oxidation cell and comprising the relevant chemical entity.

The device also comprises an electrochemical stabilization cell including at least one second working electrode, distinct from the first working electrode. This electrochemical stabilization cell is capable, when the second working electrode is subject to an electric potential, of producing a reduction of a solution.

This electrochemical stabilization cell is connected in series to the electrochemical oxidation cell so as to allow continuous reduction of the intermediate species generated in the electrochemical oxidation cell.

In alternative embodiments, the device comprises the features shown hereafter, which may be considered alone or in any combination.

The electrochemical oxidation cell and/or the electrochemical stabilization cell comprises a counter-electrode placed parallel to the corresponding working electrode and maintained spaced apart from the latter by means of a spacer element, such as a silicone gasket.

Preferably, the thickness of the spacer element is comprised between 0.4 and 1.1 mm.

In the case when at least the electrochemical stabilization cell comprises a counter-electrode, the face of this counter-electrode facing the second working electrode is covered with a porous film.

The working electrodes and/or the counter-electrode(s) are of a substantially rectangular shape.

The electrochemical oxidation cell and/or the electrochemical stabilization cell comprise a pseudo-reference electrode.

Preferably, the pseudo-reference electrode(s) is(are) placed on one of the faces of the respective working electrodes, preferably on all or part of the perimeter of one of the faces of these working electrodes, and electrically insulated from the latter by respective insulating layers.

These insulating layers are for example deposited by screen printing.

The device comprises a body, this body comprises first and second housings intended to receive the oxidation and stabilization electrochemical cells, respectively.

These first and second housings are formed by two spaces positioned on either side of an « H-shaped » central element.

The body is closed by an upper plate on the side of the counter-electrodes, and by a lower plate on the side of the working electrodes.

The upper plate is provided with two orifices in its portion which covers the electrochemical oxidation cell. One of these orifices forms an inlet orifice in the electrochemical oxidation cell. The other one forms an outlet orifice of the electrochemical oxidation cell.

This upper plate is also provided with two other orifices in its portion which covers the electrochemical stabilization cell. One of these orifices forms an inlet orifice in the electrochemical stabilization cell. The other one forms an outlet orifice of the electrochemical stabilization cell.

The outlet orifice of the electrochemical oxidation cell is connected to the inlet orifice in the electrochemical stabilization cell.

The lower plate is provided with two attachment elements able to allow attachment of the first and second working electrodes, respectively.

Thus, the device of the invention allows synthesis of the intermediate species in a sufficient amount, notably for conducting structural analyses or further pharmacological and/or toxicological tests.

The invention also relates, according to a second aspect, to a method for synthesizing intermediate species of a chemical entity electrochemically.

The method comprises a step for generating intermediate species by oxidation of a solution containing the chemical entity in an electrochemical oxidation cell.

The method also comprises a step for stabilizing the intermediate species generated by reduction in an electrochemical stabilization cell distinct from and connected in series with, the electrochemical oxidation cell.

Thus, the method is simple, requires not many manipulations and allows synthesis and stabilization in sufficient amounts of the main intermediate entities stemming from the oxidation of a molecule of interest.

BRIEF DESCRIPTION OF THE DRAWING

Other features and advantages of the invention will become more clearly apparent upon reading the description hereafter of a preferred alternative embodiment of the invention, which is given as a non-limiting example and with reference to the appended drawing.

FIG. 1 is an exploded view of a device according to the invention.

DETAILED DESCRIPTION

The device comprises two electrochemical cells (A) and (B) which will be housed in the housing 1 and 1' of a body (C), respectively.

In the example illustrated in the FIGURE, the two electrochemical cells (A) and (B) are housed on either side of a central "H-shaped" central element 2 which delimits both housings 1 and 1'.

The body (C) is closed by an upper plate 3 and a lower plate 4. The central element 2 is hemmed in between the upper plate 3 and the lower plate 4. The upper plate 3, central element 2 and lower plate 4 assembly may be maintained together by one or several attachment elements such as screws not shown in the FIGURE for the sake of clarity (only the axis and the through-holes have been illustrated in the upper plate 3, the central element 2 and the lower plate 4).

Alternatively, two distinct upper plates may be used for closing the body (C) respectively at either one of the two electrochemical cells (A) and (B). Also, two distinct lower plates may be used for closing the body (C) respectively at either one of the two electrochemical cells (A) and (B).

The first electrochemical cell (A) gives the possibility, when it is subject to an electric potential, of generating intermediate species of a chemical entity by oxidizing a solution introduced inside and which contains this chemical entity.

This electrochemical oxidation cell (A) comprises a working electrode 5 which preferably is of a substantially rectangular shape, with an extension 6 forming a connector 6 allowing connection of the working electrode 5 to a potentiostat.

A counter-electrode 7, also preferably with a substantially rectangular shape, is positioned facing the working electrode 5, parallel to the latter. This counter-electrode 7 is provided with an extension 8 forming a connector 8 allowing it to be connected to the potentiostat.

The working electrode 5 and the counter-electrode 7 are maintained spaced apart from each other by a spacer element 9, which may for example be of the silicone gasket type.

A spacing preferably comprised between 0.4 and 1.1 mm, or even between 0.5 and 1 mm will be selected.

Thus, the gap maintained between the working electrode 5 and the counter-electrode 7 via the spacer element 9 forms a space in contact both with the working electrode 5 and with the counter-electrode 7, which may receive the solution introduced into the electrochemical oxidation cell (A) so as to be subjected therein to oxidation or oxidation-reduction.

As illustrated in the FIGURE, a pseudo-reference electrode 10 is placed on one 5a of the faces of the working electrode 5, specifically the face 5a placed facing the counter-electrode 7.

The pseudo-reference electrode 10 is preferably placed on at least one portion of the perimeter of the face 5a of the working electrode 5, with an extension 11, at the connector 6 of the working electrode 5, which forms a connector 11 to an electric potential source.

The working electrode 5 and the pseudo-reference electrode 10 are separated by an insulating layer, preferably deposited by screen printing on the surface 5a of the working electrode 5, in order to avoid any electric contact between both of these electrodes 10 and 5.

Thus, the electrochemical oxidation cell (A) forms a compartment in which the oxidation products of a chemical entity such as a xenobiotic may be generated.

The production of the intermediate species may be obtained by successive scannings of the potentials with a rate which may range from a few mV/s to 10 V/s in a variable potential window and selected according to the redox potentials of the studied xenobiotic and of those of the generated species.

The use of potential scannings combined with a parallel arrangement of the working electrode 5 and of the counter-electrode 7 gives the possibility of obtaining Faradic processes (anode and cathode processes) of variable duration and alternated on both electrode surfaces facing each other.

This gives the possibility of obtaining a mixture of oxidized and reduced products. This method is very useful in the case of molecules which may be subject to an electrochemical cleavage (N-dealkylation, S-dealkylation, O-dealkylation, etc.) followed by the formation of unstable species in their oxidized forms such as quinones, quinone-imines or quinone-methide.

By alternating the anode and cathode processes by scanning of the potentials, it is possible to minimize the hydrolysis reaction of certain quinone-imines or quinone-methides into benzoquinone.

The second electrochemical cell (B), or electrochemical stabilization cell (B), when it is subject to an electrochemical potential allows reduction of a solution.

The structure of this electrochemical stabilization cell (B) is symmetrical with that of the electrochemical oxidation cell (A), with respect to the central element 2 of the body (C).

Therefore in this electrochemical stabilization cell (B), the same elements are again found as those described relatively to the electrochemical oxidation cell (A), i.e.: the working electrode 5' of a substantially rectangular shape with its connector 6'; the pseudo-reference electrode 10' with its connector 11', on the perimeter and at the surface 5a' of the working electrode 5'; the counter-electrode 7' of a substantially rectangular shape with its connector 8', facing the working electrode 5'; the spacer element 9' between the working electrode 5' and the counter-electrode 7', defining a space which may receive a solution introduced into the electrochemical stabilization cell (B) so as to be subject therein to reduction or oxidation-reduction.

Preferably, the counter-electrode 7' of the electrochemical stabilization cell (B) is entirely covered with a porous film on its surface facing the working electrode 5', which allows minimization of the Faradic anode processes in this electrochemical stabilization cell (B).

The working electrodes 5, 5' and counter-electrodes 7, 7' are preferably prepared by physical or chemical depositions by using plasma reactors or further via screen printing processes.

In both cases, a conductive film is deposited on a ceramic or stainless steel substrate. The electrode materials used (of the film type) are preferably the following: carbon, graphite, platinum and gold.

The pseudo-reference electrodes 10, 10', as for them are preferably prepared from a composite silver (Ag) or palladium (Pd) ink.

The arrangement of the whole of the electrodes within each electrochemical cell (A) and (B), substantially parallel with respect to each other, gives the possibility of ensuring a continuous flow of the solution to be electrolyzed inside these cells.

The electrochemical oxidation cell (A) and the electrochemical stabilization cell (B) are connected in series with each other.

In the example illustrated in the FIGURE, this series connection is notably obtained by a set of orifices in the upper plate 3 closing the body (C).

Thus, this upper plate 3, placed on the side of the counter-electrodes 7, 7' is provided with an inlet orifice 12 allowing introduction of a solution into the electrochemical oxidation cell (A), and an outlet orifice 13 allowing outflow of a solution introduced into the electrochemical oxidation cell (A) after this solution has been subject to oxidation in this electrochemical oxidation cell (A).

Moreover, the upper plate 3, is provided with an inlet orifice 12' allowing introduction of a solution into the electrochemical stabilization cell (B), and with an outlet orifice 13' allowing outflow of a solution introduced into the electrochemical stabilization cell (B) after this solution has been subject to reduction in this electrochemical stabilization cell (B).

A connection element 14 connects the outlet orifice 13 of the electrochemical oxidation cell (A) to the inlet orifice 12' of the electrochemical stabilization cell (B).

In order to facilitate the maintaining of the connection element 14 in position, it is possible to use end pieces 13a, 12a' such as pierced screws which will be screwed through one of their ends into the respective orifices 13, 12' and which receive through their other end the respective ends of the connection element 14.

The principle may be the same for the element 15 allowing the solution to be brought into the electrochemical oxidation cell (A) via an end piece 12a in the orifice 12, as well as for the element 16 allowing discharge of the solution of the electrochemical stabilization cell (B) via an end piece 13a' in the orifice 13'.

Preferably, a sealing element 17 is placed in the electrochemical oxidation cell (A), between the upper plate 3 and the counter-electrode 7. This sealing element 17 is provided with two through-holes 17a and 17b facing the inlet orifice 12 and the outlet orifice 13, respectively, these through-holes 17a and 17b moreover respectively opening into the holes 7a and 7b of the counter-electrode 7.

Also, and also preferably, a sealing element 17' is placed in the electrochemical stabilization cell (B), between the upper plate 3 and the counter-electrode 7'. This sealing element 17' is provided with two-through holes 17a' and 17b' facing the inlet orifice 12' and the outlet orifice 13', respectively, these through-holes 17a' and 17b' moreover respectively opening into holes 7a' and 7b' of the counter-electrode 7'.

Preferably, attachment elements 18, 18' will for example be inserted by screwing, into the lower plate 4, on the side of the working electrodes 5, 5', so as to ensure attachment of these working electrodes 5 and 5' in their respective electrochemical cells (A) and (B).

Thus, the electrochemical stabilization cell (B), connected in series to the electrochemical oxidation cell (A), forms a cathode compartment (B) allowing electrochemical reduction of the oxidized species generated in the electrochemical oxidation cell (A). This electrochemical reduction in turn gives the possibility of stabilizing these oxidized species in their reduced form and thus recovering them in a sufficient amount.

An application of the device and of the method as described above to the oxidative degradation of a β-blocking agent such as the acebulotol molecule gave the results presented hereafter.

The acebulotol introduced as a continuous flow into the electrochemical oxidation cell (A) undergoes an irreversible anode cleavage reaction.

Successive scanning of the potentials at a rate of more than 1 V/s in a potential window from −0.4 to 0.9 V vs. Pd/H$_2$, not only allows formation of the unstable species quinone-imine but also that of its reduced state 222 in a significant amount.

Indeed, the working electrode 5 and the counter-electrode 7 placed parallel with respect to each other in a continuous flow of the solution to be electrolyzed, are the centre of Faradic processes both anode and cathode processes which take place in the electrochemical oxidation cell (A), as schematized below:

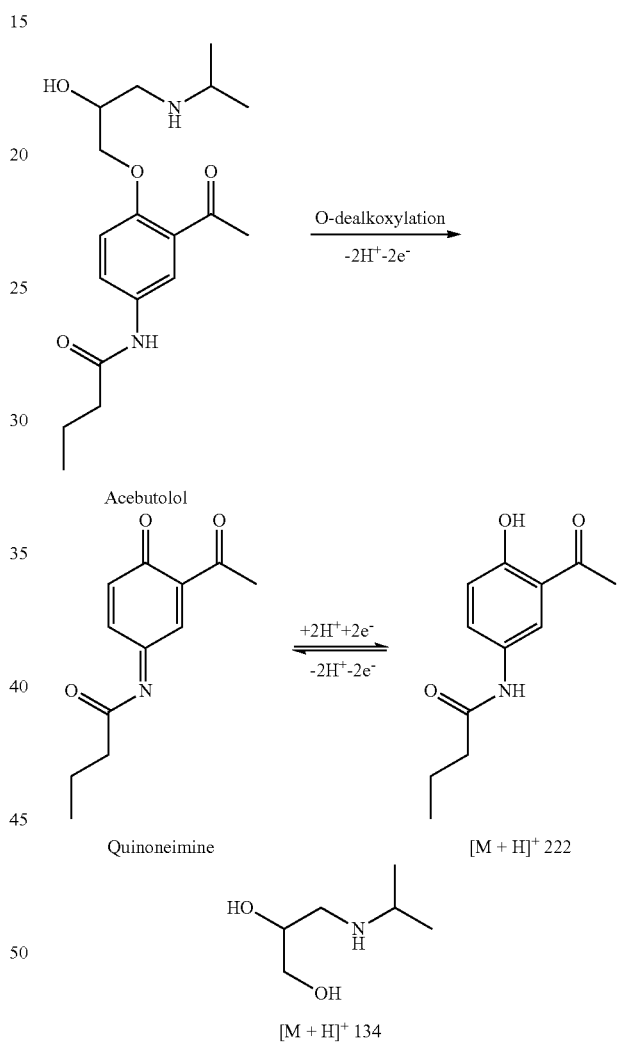

Thus, the stability of the unstable quinone-imine species is increased, and the duration of the cathode processes occurring in the electrochemical stabilization cell (B) is reduced.

Indeed, the electrochemical stabilization cell (B) allows continuous reduction of the quinone-imine species gradually during its formation in the electrochemical oxidation cell (A).

At the end of the synthesis, the intermediate species is recovered in stable form m/z 222, which is a species which is easier to isolate in a sufficient amount, at a scale of hundreds of mg, with a yield which may be of the order of 47%.

It is recalled that the whole of the description above is given as an example and is not a limitation of the invention.

In particular, the shape of the electrodes is not a limitation of the invention, even if the substantially rectangular shape is preferred for the working electrodes 5, 5' and the counter-electrodes 7, 7'.

Also, the shape of the housing 1, 1' respectively receiving the electrochemical oxidation (A) and stabilization (B) cells and the shape of the central element 2 of the body (C) of the device, are not limitations of the invention.

The invention claimed is:

1. A device for synthesizing intermediate species of a chemical entity electrochemically, comprising an electrochemical oxidation cell (A) including at least one first working electrode and a first counter-electrode, and being capable, when said first working electrode and counter-electrode are subject to an electric potential, of generating said intermediate species by oxidation of a solution introduced into said electrochemical oxidation cell (A) and comprising said chemical entity, said device also comprising an electrochemical stabilization cell (B) including at least one second working electrode and a second counter-electrode, and being capable, when said second working electrode and counter-electrode are subject to an electric potential, of achieving reduction of a solution, this said electrochemical stabilization cell (B) being connected in series to the electrochemical oxidation cell (A), wherein the first working electrode and counter-electrode are positioned substantially parallel with respect to each other, and maintained spaced apart from each other by means of a first spacer element, so as to each have a surface facing each other, and the second working electrode and counter-electrode are respectively distinct from the first working electrode and counter-electrode, so as to allow continuous reduction in the electrochemical stabilization cell (B) of the intermediate species generated in the electrochemical oxidation cell (A) by scanning, in a given window of potentials, electric potentials applied to the first working electrode and counter-electrode, the device further comprising a body (C) comprising first and second housings intended to receive the electrochemical oxidation (A) and stabilization (B) cells, respectively, the first and second housings being formed by two spaces positioned on either side of an "H-shaped" central element.

2. The device according to claim 1, wherein the thickness of the first spacer element is comprised between 0.4 and 1.1 mm.

3. The device according to claim 1, wherein at least one of the working electrodes and the counter-electrodes are of a substantially rectangular shape.

4. The device according to claim 1, wherein at least one of the electrochemical oxidation cell (A) and the electrochemical stabilization cell (B) comprise a pseudo-reference electrode.

5. The device according to claim 4, wherein at least one of the pseudo-reference electrodes are placed on one of the faces of the respective working electrodes and electrically insulated from the latter by respective insulating layers.

6. The device according to claim 1, wherein the body (C) is closed by an upper plate on the side of the counter-electrodes, and by a lower plate on the side of the working electrodes.

7. The device according to claim 6, wherein the upper plate is provided with an inlet orifice in, and with an outlet orifice of the electrochemical oxidation cell (A), on the other hand and an inlet orifice in, and with an outlet orifice of, the electrochemical stabilization cell (B), said outlet orifice of the electrochemical oxidation cell (A) being connected to said inlet orifice in the electrochemical stabilization cell (B).

8. The device according to claim 6, wherein the lower plate is provided with two attachment elements capable of allowing attachment of the first and second working electrodes, respectively.

9. A method for synthesizing intermediate species of an chemical entity electrochemically comprising a step for generating intermediate species by oxidation of a solution containing said chemical entity in an electrochemical oxidation cell (A), and a step for stabilizing the intermediate species generated by reduction in an electrochemical stabilization cell (B) connected in series with the electrochemical oxidation cell (A), wherein the generation of the intermediate species in the electrochemical oxidation cell (A) comprises the scanning, in a given window of potentials, of electric potentials applied to a first working electrode and a first counter-electrode placed substantially parallel with respect to each other, and maintained spaced apart from each other by means of a first spacer element, so as to each have a surface facing each other, and the stabilization in the electrochemical stabilization cell (B), of the intermediate species generated in the electrochemical oxidation cell (A), comprises continuous reduction of these intermediate species by applying an electric potential to a second working electrode and a second counter-electrode respectively distinct from the first working electrode and counter-electrode, the device further comprising a body (C) comprising first and second housings intended to receive the electrochemical oxidation (A) and stabilization (B) cells, respectively, the first and second housings being formed by two spaces positioned on either side of an "H-shaped" central element.

10. The device according to claim 5, wherein the insulating layers are screen printing deposited layers.

11. The device according to claim 5, wherein the pseudo-reference electrodes are placed on all or part of the perimeter of one of the faces of the respective working electrodes.

* * * * *